United States Patent
Hughes

(10) Patent No.: US 6,514,238 B1
(45) Date of Patent: Feb. 4, 2003

(54) METHOD FOR PREPARATION AND TRANSPLANTATION OF VOLUTE GRAFTS AND SURGICAL INSTRUMENT THEREFOR

(75) Inventor: Stephen E. Hughes, Delmar, NY (US)

(73) Assignee: Photogenesis, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/464,054

(22) Filed: Jun. 5, 1995

Related U.S. Application Data

(60) Division of application No. 08/057,144, filed on Apr. 30, 1993, now abandoned, which is a continuation-in-part of application No. 08/033,105, filed on Mar. 16, 1993, now abandoned, which is a continuation-in-part of application No. 07/566,966, filed on Aug. 13, 1990, now abandoned, which is a continuation-in-part of application No. 07/394,377, filed on Aug. 14, 1989, now abandoned.

(51) Int. Cl.[7] ............... A61B 17/00; A61M 35/00; A61M 31/00
(52) U.S. Cl. ............... 606/1; 606/166; 604/239; 604/294; 604/289; 604/59; 604/57
(58) Field of Search ............... 604/239, 294, 604/59, 57, 272, 289, 290, 295, 187; 606/166; 623/5

(56) References Cited

U.S. PATENT DOCUMENTS

| | | |
|---|---|---|
| 5,292,802 A | 3/1994 | Rhee |
| 5,308,889 A | 5/1994 | Rhee |
| 5,322,691 A | 6/1994 | Darouger et al. |
| 5,323,788 A | 6/1994 | Silvestrini et al. |
| 5,324,260 A | 6/1994 | O'Neill et al. |
| 5,817,075 A * | 10/1998 | Giungo ............... 604/294 |

OTHER PUBLICATIONS

A. Adolph; "Function and Structure in Isolated Subretinal Transplants", *Invest. Opthal. Vis. Sci.*, 34:1096, 1993.

R. Aramant; "Xenografting Human Fetal Retina to Adult Rat Retina", *Suppl., Invest. Ophthal. Vis. Sci.*, 31:594, 1990.

R. Aramant; "The Fate of Retinal Ganglion Cells, Retrogradely Labelled with Fluorogold and Transplanted to Rat Retina", *Suppl., Ivest. Opthal. Vis. Sci.*, 32:983, 1991.

(List continued on next page.)

*Primary Examiner*—Linda C. M. Dvorak
*Assistant Examiner*—Sonya Harris
(74) *Attorney, Agent, or Firm*—Brinks Hofer Gilson & Lione; Daniel B. Schein, Esq.

(57) ABSTRACT

A method of transplanting a graft in the subretinal area of a host eye comprises preparing the graft by harvesting from the donor tissue a population of cells in a manner that maintains the population of cells in the same organization and cellular polarity as is present in normal tissue of that type. The population of cells are of a sheet-like form and are assembled with a relatively thin flexible pliable carrier composed of a non-toxic flexible composition which substantially dissolves at body temperature to form a graft. The graft is sufficiently flexible and pliable to be coiled to form a volute without disturbing the organization and polarity of the cells. The method further comprises coiling the graft to form a volute with the convolutions of the volute free of one another for subsequent uncoiling of the graft substantially to its original sheet-like form. An incision is made in the host eye for insertion of the volute. The incision in the eye is smaller than the incision that would be required for insertion of the graft in its uncoiled sheet-like form. The volute is inserted one end first into the host eye through the incision and transported to a position between the retina and the underlying tissue. The volute uncoils after its insertion to lie in sheet-like form between the retina and the underlying tissue of the host eye. The incision is then closed.

9 Claims, 6 Drawing Sheets

OTHER PUBLICATIONS

R. Aramant; "Tracing of Connections Between Retinal Transplants and Host Retina with DiI", *Invest. Opthal. Vis. Sci.*, 34:1096, 1993.

ARVO "Abstract Packet for Annual Meeting" Sarasota, Florida (May 2–May 7, 1993).

ARVO "Conference Brochure for Annual Meeting" Sarasota, Florida (May 2–May 7, 1993).

N. Bhatt; "Transplantation of Human Retinal Pigment Epithelial Cells Into Rabbits", *Invest. Opthal. Vis, Sci.*, 34:1919–75, 1993.

A. Bonds; "Visually Evoked Potentials and Deoxyglucose Studies of Monocularly Deprived Cats", *Suppl., Invest. Opthal. Vis. Sci.*, 18:225–226, 1980.

D. Cameron; "The Cone Photoreceptor Mosaic of the Green Sunfish", *Soc. Neuroscience*, 18:838, 1992.

P. Custis; "Clinical Angiographic and Histopathologic Correlations in Surgically Removed Subfoveal Choroidal Neovascularization", *Invest. Opthal. Vis. Sci.*, 34:834, 1993.

M. del Cerro; "Selective Transplantation of Enriched Cell Populations Derived from Immature Rat Retina", *Suppl. Invest. Opthal. Vis. Sci.*, 30:208, 1989.

L. Del Priore; "Transplantation of Retinal Pigment Epithelium (RPE) Onto Bruch's Membrane in Organ Culture", *Suppl., Invest. Opthal. Vis. Sci.*, 33:1127, 1992.

L. Del Priore; "Experimental and Surgical Aspects of Retinal Pigment Epithelial Cell Transplantation", *Eur. J. Implant Ref. Surg.*, 5:128–132, 1993.

L. Del Priore; "Differential Ability of Aged Versus Young Human Bruch's Membrane to Support Repopulation By Healthy RPE", *Invest. Opthal. Vis. Sci.*, 34:834, 1993.

J. Du; "Long Term Survivalof Infant Versus Adult Photoreceptor Transplants Labeled by Tritiated Thymidine", *Suppl., Invest. Opthal. Vis. Sci.*, 32:983, 1991.

J. Du; "Neonatal Mouse Photoreceptor Transplants Replace the Photoreceptor Layer of the Host", *Invest. Opthal. Vis. Sci.*, 34:1096, 1993.

S. Edwards; "Light–Regulated Portein Phosphatase Activity in *Limulus* Ventral Photoreceptors", *Soc. Neuroscience*, 16:405, 1990.

O. Ferguson; "Effect of Genetic Disparity on Photoreceptor Transplant Survival", *Suppl., Invest. Opthal. Vis. Sci.*, 32:983, 1991.

O. Fischer; "Photoreceptor Topography in the Retinae of Anubis Baboons", *Soc. Neuroscience*, 18:838, 1992.

C. Garcia; "Comparison of Allogeneic and Syngeneic RPE Transplants in Renal Subcapsular Space", *Invest. Opthal. Vis. Sci.*, 34:1112, 1993.

E. Gao; "Low Immunogenicity of Neonatal Murine Photoreceptor Cells for Cytotoxic T Lymphocytes in Mice", *Suppl., Invest. Opthal. Vis. Sci.*, 33:1285, 1992.

M. Gelanze; "Survival of Photoreceptors Transplanted to the Subretinal Space of Adult RCS Rats", *Suppl. Invest. Opthal. Vis. Sci.*, 30:308, 1989.

P. Gouras; "Transplanted Photoreceptors Form Mature Outer Segments in Degenerate rd Mouse Retina", *Invest. Opthal. Vis. Sci.*, 33:1128, 1992.

P. Gouras; "Anatomy and Physiology of Photoreceptor Transplants in Degenerate C3H Mouse Retina", *Invest. Opthal. Vis. Sci.*, 34:1096, 1993.

S. Hughes; "Whole Cell Recordings of Isolated Retinal Pigment Epithelial Cells of the Frog", *Soc. Neuroscience Abstr.*, 17:1301, 1987.

S. Hughes; "Differential Survival of Sensory Elements in Intracranial Otic Transplants", *Soc. Neuroscience*, 17:1138, 1991.

S. Hughes; "Quantification of Synapses in Light–Damaged Retina Reconstructed by Transplantation of Photoreceptors", *Suppl., Invest. Opthal. Vis. Sci.*, 32:1058, 1992.

S. Hughes; "Explorations of Otic Transplantation", *Experimental Neurology*, 115:37–43 1992.

G. Jacobs; "An Ultraviolet–Sensitive Cone in the Gerbil Retina", *Soc. Neuroscience*, 18:838, 1992.

L. Jiang; "Intraocular Retinal Transplantation in Retinal Degeneration (rd/rd) Murine Strains", *Suppl., Invest. Opthal. Vis. Sci.*, 30:208, 1989.

H. Kaplan; "Retinal Pigment Epithelium Regeneration in the Non–Human Primate", *Suppl., Invest. Opthal. Vis. Sci.*, 33:1127, 1992.

J. Kordower; "Fetal Monkey Retina Transplanted into Adult Rat Eyes", *Suppl. Invest. Opthal. Vis. Sci.*, 30:208, 1989.

B. Kruszewska; "Ultrastructure and Transduction in the Caudal Photoreceptor of Crayfish", *Soc. Neuroscience*, 16:405, 1990.

M. LaVail; "RPE Cell Transplantation in RCS Rats: Normal Metabolism in Rescued Photoreceptors", *Suppl., Invest. Opthal. Vis. Sci.*, 33:1127, 1992.

J. Lee; "Transplantation of Cultured Retinal Pigment Epithelium to Rabbit Retina Injured by Sodium Iodate", *Suppl., Invest. Opthal. Vis. Sci.*, 33:1127, 1992.

Y. Liu, "Photoreceptors Inner and Outer Segments in Transplanted Retina", *Soc. Neuroscience*, 16:405, 1990.

Y. Liu; "Transplantation of Confluent Sheets of Adult Human RPE", *Invest. Opthal. Vis. Sci.*, 33:1128, 1993.

Y. Liu; "Transplantation of Confluent Sheets of Adult Human and Rat RPE on a Thin Substrate", *Invest. Opthal. Vis. Sci.*, 34:1112, 1993.

R. Lopez; "Transplantation of Human RPE Cells into the Monkey", *Suppl., Invest. Opthal. Vis. Sci.*, 31:594, 1990.

R. Lund; "Axonal Outgrowth from Transplanted Retinae is Stimulated by Appropriate Target Regions", *Arvo Abstracts* 288.

J. McCulley; "Keratoplasty with Cultured Endothelium on Thin Membranes," *ARVO Abstracts, Suppl., Invest. Opthal. Vis. Sci.*, 9–10:30, Apr. 1979.

J. McCulley; "Corneal Endothelial Transplantation", *ARVO Abstracts, Suppl., Invest. Opthal. Vis. Sci.*, 9–10:30, Apr. 1979.

J. McCulley; "A Gelatin Membrane Substrate for the Transplantation of Tissue Cultured Cells", *Transplantation*, vol. 29, No. 6, pp. 498–99, Jun. 1980.

T. Moritera; Transplants of Monolayer Retinal Pigment Epithelium Grown on Biodegradable Membrane in Rabbits, *Invest. Opthal. Vis. Sci.*, 34:1919–75, 1993.

J. Muller; "Morphology and Synaptic Inputs to Lucifer Yellow Injected Bipolar Cells In Rat Retinal Slices", *Soc. Neuroscience*, 17:1013, 1991.

J. Muller; "Rod and Cone Inputs to Bipolar Cells in the Rat Retina.", *Soc. Neuroscience*, 17:1013, 1991.

J. Mueller; "Autotransplantation of Retinal Pigment Epithelium in Intravitreal Diffusion Chamber", *Retinal Pigment Epithelium*, Part II, vol. 80, No. 3, p. 530, 1993.

M. Nasir; "Choriocapillaris Atrophy as a Complication of Surgical Excision of Choroidal Neovascular Membranes", *Invest. Opthal. Vis. Sci.*, 34:834, 1993.

H. Petry; "Immunocytochemical Identification of Photoreceptor Populations in the Retinas of Normal and Red–Light-Reared Tree Shrews", *Soc. Neuroscience,* 18:838, 1992.

J. Radel; "Quantification of Light–Activated Pupilloconstriction in Rats Mediated by Intracranially Transplanted Retinae", *Suppl., Invest. Opthal. Vis. Sci.,* 32:983, 1991.

P. Raymond; "Progenitor Cells in Outer Nuclear Layer of Goldfish Retina That Normally Produce Only Rods Produce Other Neurons During Retinal Degeneration", *Suppl., Invest. Opthal. Vis. Sci.,* 32:983, 1991.

S. Schuschereba; "Retinal Cell and Photoreceptor Transplantation Between Adult New Zealand Red Rabbit Retina", *Experimental Neurology,* 115:95–99, 1992.

A. Seaton; "Inhibition of Neovascularization by the Transplantation of Healthy Retinal Pigment Epithelial Cells into the RCS Rat", *Suppl., Invest. Opthal. Vis. Sci.,* 32:983, 1991.

H. Sheedlo; "Photoreceptor Cell Rescue by REP–Cell Grafts in RCS Rats at Early and Late Stages of Retinal Dystrophy", *Suppl., Invest. Opthal. Vis. Sci.,* 30:208, 1989.

M. Silverman; "Deoxyglucose Mapping of Orientation and Spatial Frequency in Cat Visual Cortex", *Suppl., Invest. Opthal. Vis. Sci.,* 18:225, 1980.

M. Silverman; "Deoxyglucose Mapping of Orientation in Cat Visual Cortex", *Recent Advances in Vision, Optical Society of America Technical Digest,* SA13, 1980.

M. Silverman; "The Retinotopic Organization of Cat Striate Cortex.", *Suppl., Invest. Opthal. Vis. Sci.,* 22:105, 1982.

M. Silverman; "Photoreceptor Rescue in the RCS Rat Without Pigment Epithelial Transplantation", *Soc. Neuroscience,* 15:115, 1989.

M. Silverman; "Photoreceptor Transplantation to Dystrophic Retina", *Retinal Degenerations* (ed. by R. Anderson, R.E.), CRC Press, Inc., Ch. 29, pp 321–335, 1991.

M. Silverman; Confidential letter dated Oct. 7, 1991 to Gholam A. Peyman, M.D. and attachents.

M. Silverman; "Restoration of the Pupillary Reflex by Photoreceptor Transplantation", *Suppl., Invest. Opthal. Vis. Sci.,* 32:983, 1991.

M. Silverman; "Photoreceptor Transplantation: Anatomic Electrophysiologic and Behavorial Evidence for the Functional Reconstruction of Retinas Lacking Photoreceptors", *Soc. Neuroscience,* 17:12, 1991.

M. Silverman; "Transplantation of Retinal Photoreceptors to Light–Damaged Retina", *Arvo Abstracts,* 288.

T. Solomons; "Special Topic M Photochemistry of Vision", *Organic Chemistry,* 5th ed., John Wiley & Sons, Inc., pp. 1168–1171.

L. Tien; "In Search of A Receptor for Outer Segments in Rat Retinal Pigmented Epithelium", *Soc. Neuroscience,* 16:405, 1990.

R. Tootell; "Deoxglucose Mapping of Color and Spatial Frequency Organization in Monkey and Cat Cortex", *Recent Advances in Vision, Optical Society of America Tech. Digest.,* SA14, 1980.

R. Tootell; "2DG Study of Retinotopic Organization in Macaque Striate Cortex", *Suppl., Invest. Ophthal. Vis. Sci.,* 22:12, 1982.

R. Tootell; "Deoxyglucose Analysis of Retinotopic Organization in Primate Striate Cortex", *Science,* 218:902–904, 1982.

R. Tootell; "Two Methods for Flat–Mounting Cortical Tissue", *J. Neurosci. Methods,* 15:177–190, 1985.

B. Tuliusson; "Reversed Ratio of Color Specific Cones in Rabbit Retinal Transplants", *Invest. Opthal. Vis. Sci.,* 34:1096, 1993.

T. Valentino; "Transplanted Photoreceptors Form Synapses in Reconstructed RCS Rat Retina", *Soc. Neuroscience* 16:405, 1990.

T. Valentino; "Photoreceptor Sheets Isolated from the Neonatal Rat Retina Lack Synapses and Other Retinal Cells", *Soc. Neuroscience,* 18:838, 1992.

S. Vinores; "Ulstrastructural Localization of RPE Epitopes in In Situ and Clutrued RPE Cells and their Expression in Fibroblasts in Vitreous Culture", *Soc. Neuroscience,* 16:405, 1990.

C. Zucker; "Synaptic Microcircuitry of Rat Retinal Transplants Ultrastructural Observations", *Suppl., Invest. Opthal. Vis. Sci.,* 31:594, 1990.

\* cited by examiner

FIG. 17
FIG. 18
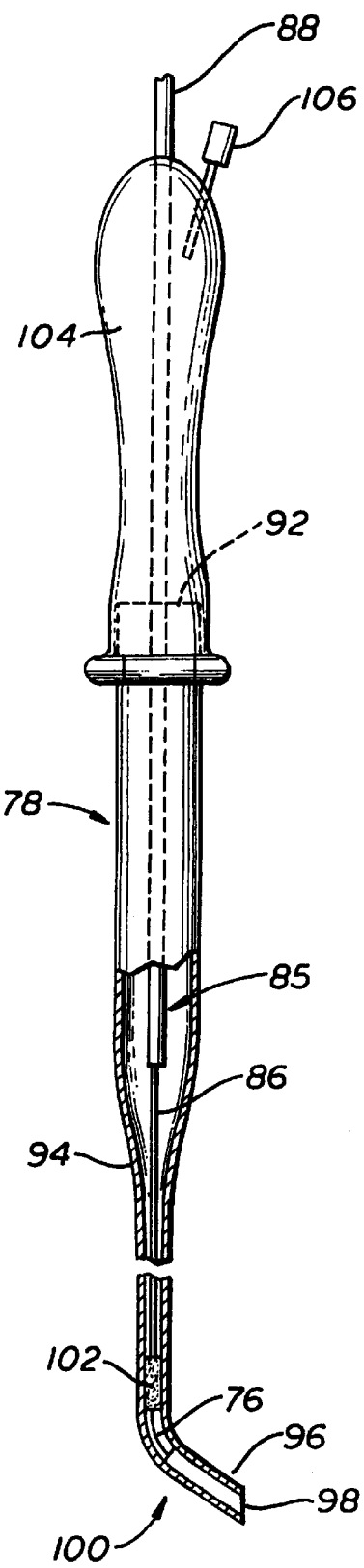
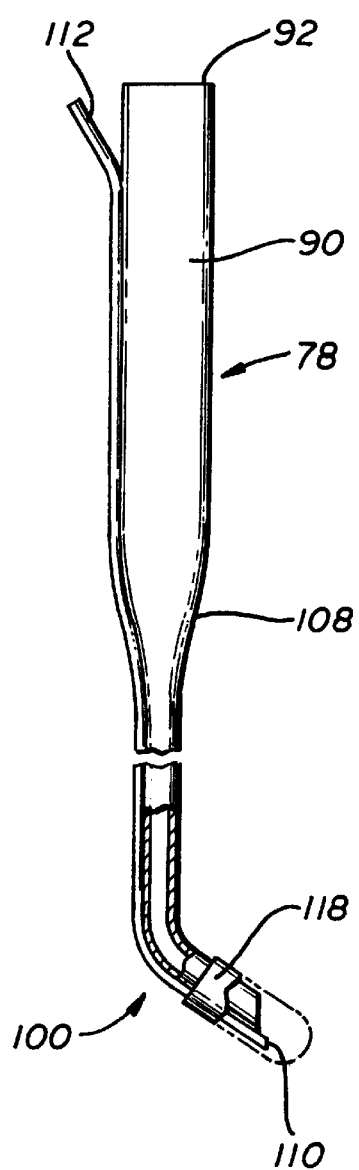

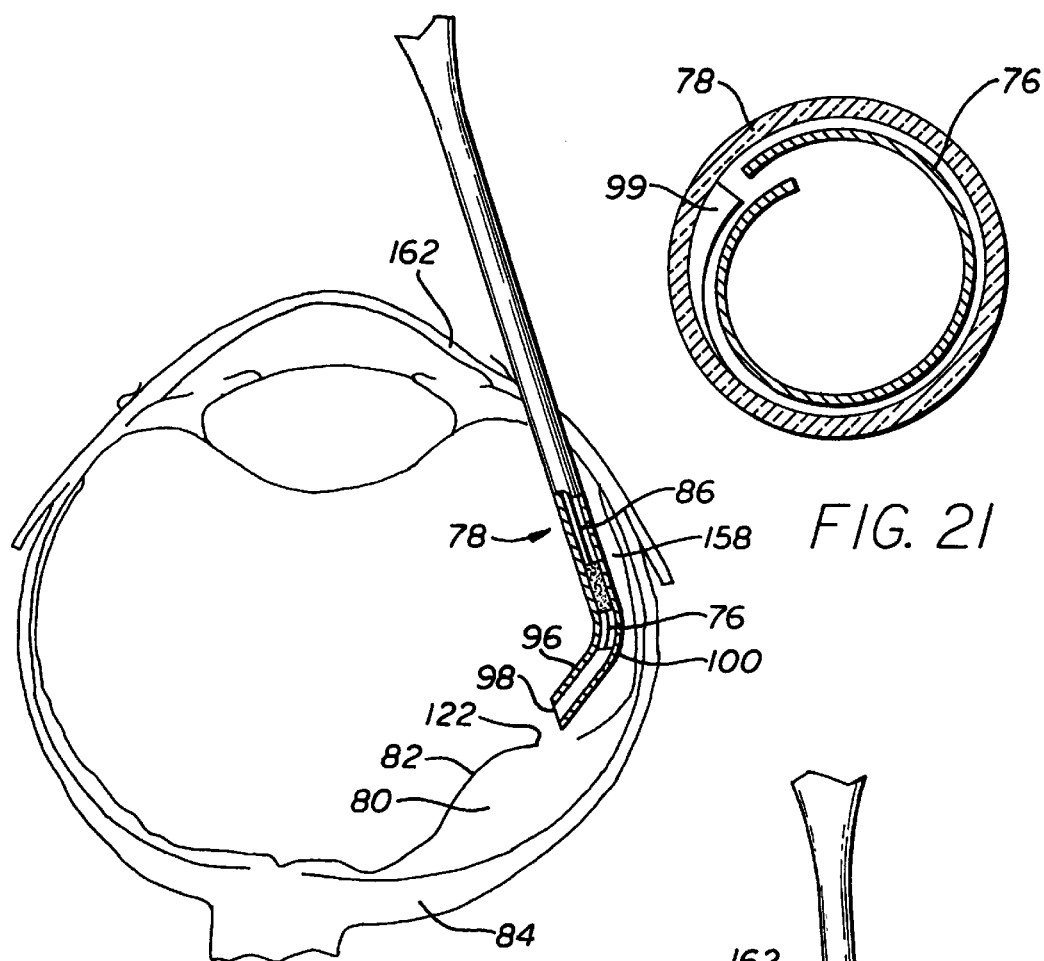
FIG. 19
FIG. 21
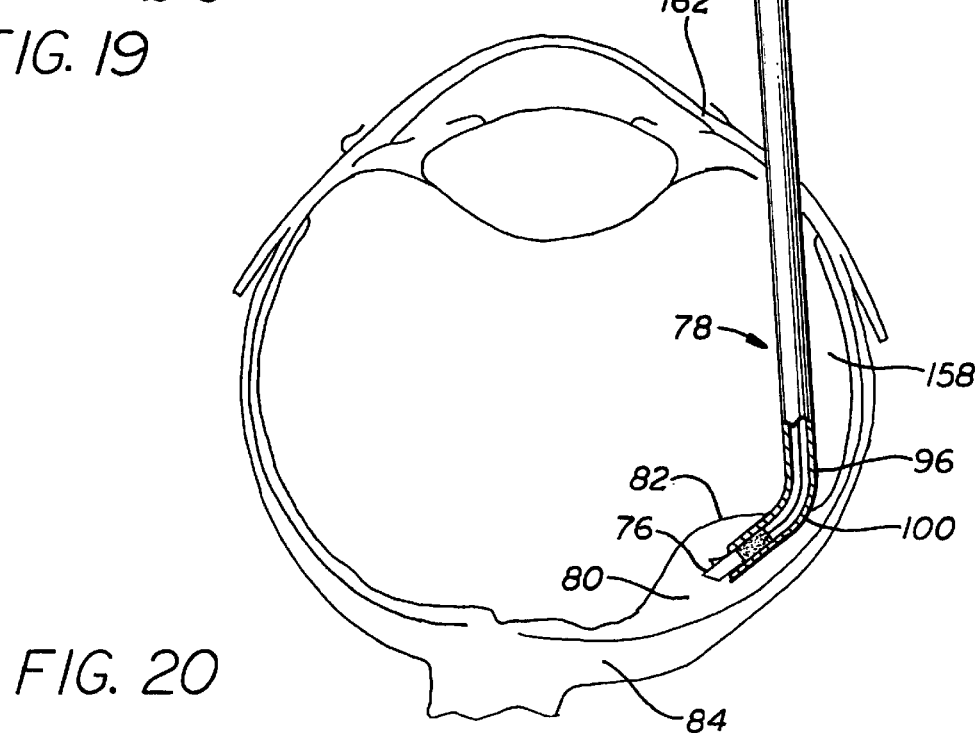
FIG. 20

METHOD FOR PREPARATION AND TRANSPLANTATION OF VOLUTE GRAFTS AND SURGICAL INSTRUMENT THEREFOR

This is a division, of application Ser. No. 08/057,144 filed Apr. 30, 1993, now abandoned, which is a continuation-in-part of application Ser. No. 08/033,105, filed Mar. 16, 1993, now abandoned and Ser. No. 07/566,966, filed Aug. 13, 1990 now abandoned, which in turn is a continuation-in-part of application Ser. No. 07/394,377 filed Aug. 14, 1989, now abandoned.

BACKGROUND OF THE INVENTION

The present invention relates in general to surgical instruments and surgical techniques. More particularly, the present invention is directed to a surgical tool for transplanting sheets of retinal cells, epithelial tissue and/or choroidal tissue in a volute configuration through a standard-sized incision in the eye, a graft for transplantation to the subretinal region of the eye, a method for preparing such grafts for transplantation and a method for reconstructing dystrophic retinas, retinal pigment epithelial layers and choroids.

The retina is the sensory epithelial surface that lines the posterior aspect of the eye, receives the image formed by the lens, transduces this image into neural impulses and conveys this information to the brain by the optic nerve. The retina comprises a number of layers, namely, the ganglion cell layer, inner plexiform layer, inner nuclear layer, outer plexiform layer, outer nuclear layer, photoreceptor inner segments and outer segments. The outer nuclear layer comprises the cell bodies of the photoreceptor cells with the inner and outer segments being extensions of the cell bodies.

The choroid is a vascular membrane containing large branched pigment cells that lies between the retina and the sclerotic coat of the vertebrate eye. Immediately between the choroid and the retina is the retinal pigment epithelium which forms an intimate structural and functional relationship with the photoreceptor cells.

Several forms of blindness are primarily related to the loss of photoreceptor cells caused by defects in the retina, retinal pigment epithelium, choroid or possibly other factors (e.g. intense light, retinal detachment, intraocular bleeding). In several retinal degenerative diseases select populations of cells are lost. Specifically, in macular degeneration and retinitis pigmentosa, the retinal photoreceptors degenerate while other cells in the retina as well as the retina's central connections are maintained. In an effort to recover what was previously thought to be an irreparably injured retina, researchers have suggested various forms of grafts and transplantation techniques, none of which constitute an effective manner for reconstructing a dystrophic retina.

The transplantation of retinal cells to the eye can be traced to a report by Royo et al., *Growth* 23: 313–336 (1959) in which embryonic retina was transplanted to the anterior chamber of the maternal eye. A variety of cells were reported to survive, including photoreceptors. Subsequently del Cerro was able to repeat and extend these experiments (del Cerro et al., *Invest. Ophthalmol. Vis. Sci.* 26: 1182–1185, 1985). Soon afterward Turner, et al. *Dev. Brain Res.* 26:91–104 (1986) showed that neonatal retinal tissue could be transplanted into retinal wounds.

In related studies, Simmons et al., *Soc. Neurosci. Abstr.* 10: 668 (1984) demonstrated that embryonic retina could be transplanted intracranially, survive, show considerable normal development, be able to innervate central structures, and activate these structures in a light-dependent fashion. Furthermore, these intracranial transplants could elicit light-dependent behavioral responses (pupillary reflex) that were mediated through the host's nervous system. Klassen et al., *Exp. Neurol.* 102: 102–108 (1988) and Klassen et al. *Proc. Natl. Acad., Sci. USA* 84:6958–6960 (1987).

Li and Turner, *Exp. Eye Res.* 47:911 (1988) have proposed the transplantation of retinal pigment epithelium (RPE) into the subretinal space as a therapeutic approach in the RCS dystrophic rat to replace defective mutant RPE cells with their healthy wild-type counterparts. According to their approach, RPE was isolated from six- to eight-day old black eyed rats and grafted into the subretinal space by using a lesion paradigm which penetrates through the sclera and choroid. A 1 ml injection of RPE (40,000–60,000 cells) was made at the incision site into the subretinal space by means of a 10 ml syringe to which was attached a 30 gauge needle. However, this method destroys the cellular polarity and native organization of the donor retinal pigment epithelium which is desirable for transplants.

del Cerro, (del Cerro et al., *Invest. Ophthalmol. Vis. Sci.* 26: 1182–1185, 1985) reported a method for the transplantation of tissue strips into the anterior chamber or into the host retina. The strips were prepared by excising the neural retina from the donor eye. The retina was then cut into suitable tissue strips which were then injected into the appropriate location by means of a 30 gauge needle or micropipette with the width of the strip limited to the inner diameter of the needle (250 micrometers) and the length of the strip being less than 1 millimeter. While del Cerro reports that the intraocular transplantation of retinal strips can survive, he notes that the procedure has some definite limitations. For instance, his techniques do not allow for the replacement of just the missing cells (e.g. photoreceptors) but always include a mixture of retinal cells. Thus, with such a transplant appropriate reconstruction of the dystrophic retina that lacks a specific population of cells (e.g., photoreceptors) is not possible.

del Cerro et al., *Neurosci. Lett.* 92: 21–26, 1988, also reported a procedure for the transplantation of dissociated neuroretinal cells. In this procedure, the donor retina is cut into small pieces, incubated in trypsin for 15 minutes, and triturated into a single cell suspension by aspirating it through a fine pulled pipette. Comparable to the Li and Turner approach discussed above, this procedure destroys the organized native structure of the transplant, including the donor outer nuclear layer; the strict organization of the photoreceptors with the outer segments directed toward the pigment epithelium and the synaptic terminals facing the outer plexiform layer are lost. Furthermore, no means of isolating and purifying any given population of retinal cells (e.g. photoreceptors) from other retinal cells was demonstrated.

It is believed by the present inventor that it is necessary to maintain the photoreceptors in an organized outer nuclear layer structure in order to restore a reasonable degree of vision. This conclusion is based on the well known optical characteristics of photoreceptors (outer segments act as light guides) and clinical evidence showing that folds or similar, even minor disruptions in the retinal geometry can severely degrade visual acuity.

SUMMARY OF THE INVENTION

Among the objects of the present invention, therefore, may be noted the provision of a method which conserves relatively large expanses of tissue harvested from a donor eye; the provision of such a method in which a relatively large expanse of harvested tissue is so formed as to enable the harvested tissue to be inserted into a standard-sized incision in the eye; the provision of such a method in which the polarity and organization of the cells at the time of harvest are maintained in the graft; and the provision of a method for implantation of grafts to the subretinal area of an eye.

Further among the several objects and features of the present invention may be noted the provision of a graft for use in the reconstruction of a dystrophic retina or rescue of endogenous photoreceptor cells of an individual afflicted with an inherited or acquired retinal disease which causes a progressive loss of rods and subsequent eventual cone dystrophy, dysfunction and/or loss; the provision of such a graft which facilitates regrowth of photoreceptor axons by maintaining the polar organization of the photoreceptor and the close proximity of their postsynaptic targets with the adjacent outer plexiform layer upon transplantation.

Further among the several objects and features of the present invention may be noted the provision of a surgical tool for use in the implantation method which forms the graft for insertion into a standard-sized incision; and the provision of a surgical tool for use in the transplantation method which allows appropriate retinotopic positioning and which protects photoreceptors, retinal pigment epithelial tissue, choroidal tissue and/or Bruch's membrane from damage prior to and as the surgical device is positioned in the eye.

Generally, the implantation method comprises coiling an implantable material which is of sheet-like form to form a volute. The convolutions of the volute are free of one another for subsequent uncoiling of the implantable material substantially to its original sheet-like form. An incision is made in the host eye for the insertion of the volute to a position between the retina and the underlying tissue of the host eye. The incision is smaller than the incision that would be required for insertion of the implantable material in its uncoiled sheet-like form. The volute is inserted one end first into the host eye through the incision to a position between the retina and the underlying tissue. The volute uncoils after its insertion to lie in sheet-like form between the retina and the underlying tissue of the host eye and the incision is closed.

Generally, the graft for implantation comprises a layer of a non-toxic flexible composition which substantially dissolves at body temperature and a material to be implanted coiled to form a volute. The volute is insertable one end first through the incision dimensioned in accordance with the cross-sectional area of the volute to a position for implantation, and then uncoiled to lie in sheet-like form at the site of implantation.

Generally, the implement for the formation of a volute comprises a tubular body open at one end and having a funnel. A carrier enters one end first in the tubular body at the open end thereof and is fed along the body into and through the funnel. The engagement of the carrier as it is fed through the funnel with an interior surface of the funnel causes the carrier to coil into the volute. The volute exits from a small end of the funnel.

Other objects and features of the invention will be in part apparent and in part pointed out hereinafter.

BRIEF DESCRIPTION OF THE DRAWINGS

FIG. 17. is a side elevational view of the instrument with a lumen attached to the outside of the instrument;

FIG. 18 is a side elevational view of the instrument with the plunger advancing the volute;

FIG. 19 is a horizontal section through an eye illustrating a pars plana surgical approach with the instrument extending partially across the eye;

FIG. 20. is a horizontal section through an eye illustrating a pars plana surgical approach with the instrument inserted into a bleb; and FIG. 21. is a horizontal section taken along line 21—21 of FIG. 16 illustrating a ramp within the instrument.

Corresponding reference characters indicate corresponding parts throughout the several views of the drawings.

DETAILED DESCRIPTION

As used herein, the term "donor" shall mean the same or different organism relative to the host and the term "donor tissue" shall mean tissue harvested from the same or different organism relative to the host.

Several forms of blindness such as retinitis pigmentosa, retinal detachment, macular degeneration, and light exposure-related blindness, are primarily related to the loss of the photoreceptors in the eye. However, destruction of the photoreceptors does not necessarily lead to the loss of the remaining retina or axons that connect the retina to the brain. Surprisingly, it has been discovered that some degree of vision can be restored by replacing damaged photoreceptors with photoreceptors harvested from a donor and which are maintained in their original organization and cellular polarity. Furthermore, as further described in co-pending application Ser. No. 08/033,105 (which is incorporated herein by reference), the transplantation of photoreceptor rods harvested from a donor eye can "rescue" endogenous cone photoreceptors within the retina and thus may restore or preserve visual sensitivity of existing cone photoreceptors. That is, it has been found that transplanted rods exert a trophic effect upon endogenous cone photoreceptors.

Figure 1:
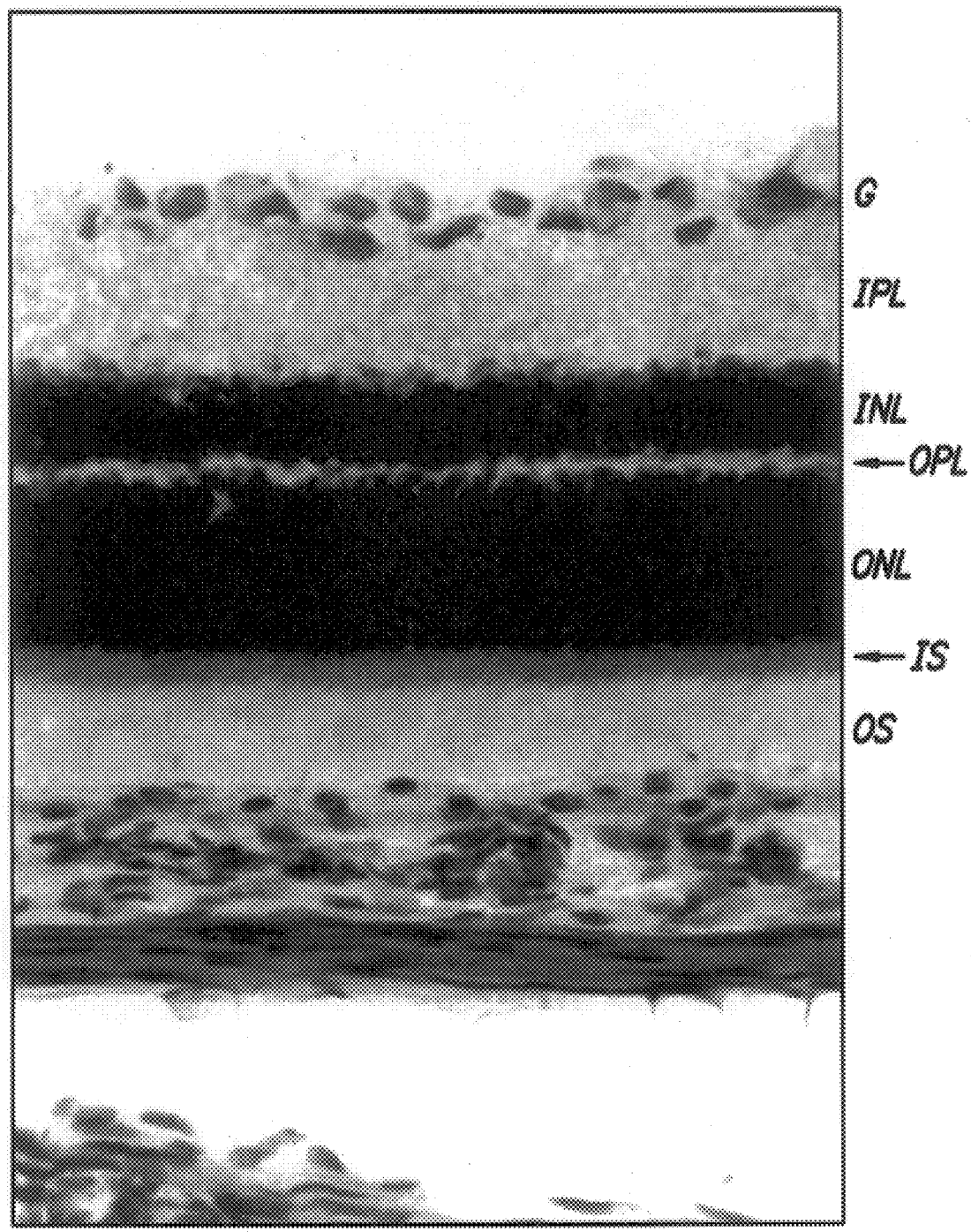
FIG. 1 is a photograph of a cryostat section of normal rat retina as set forth in Example 1.
Figure 2:
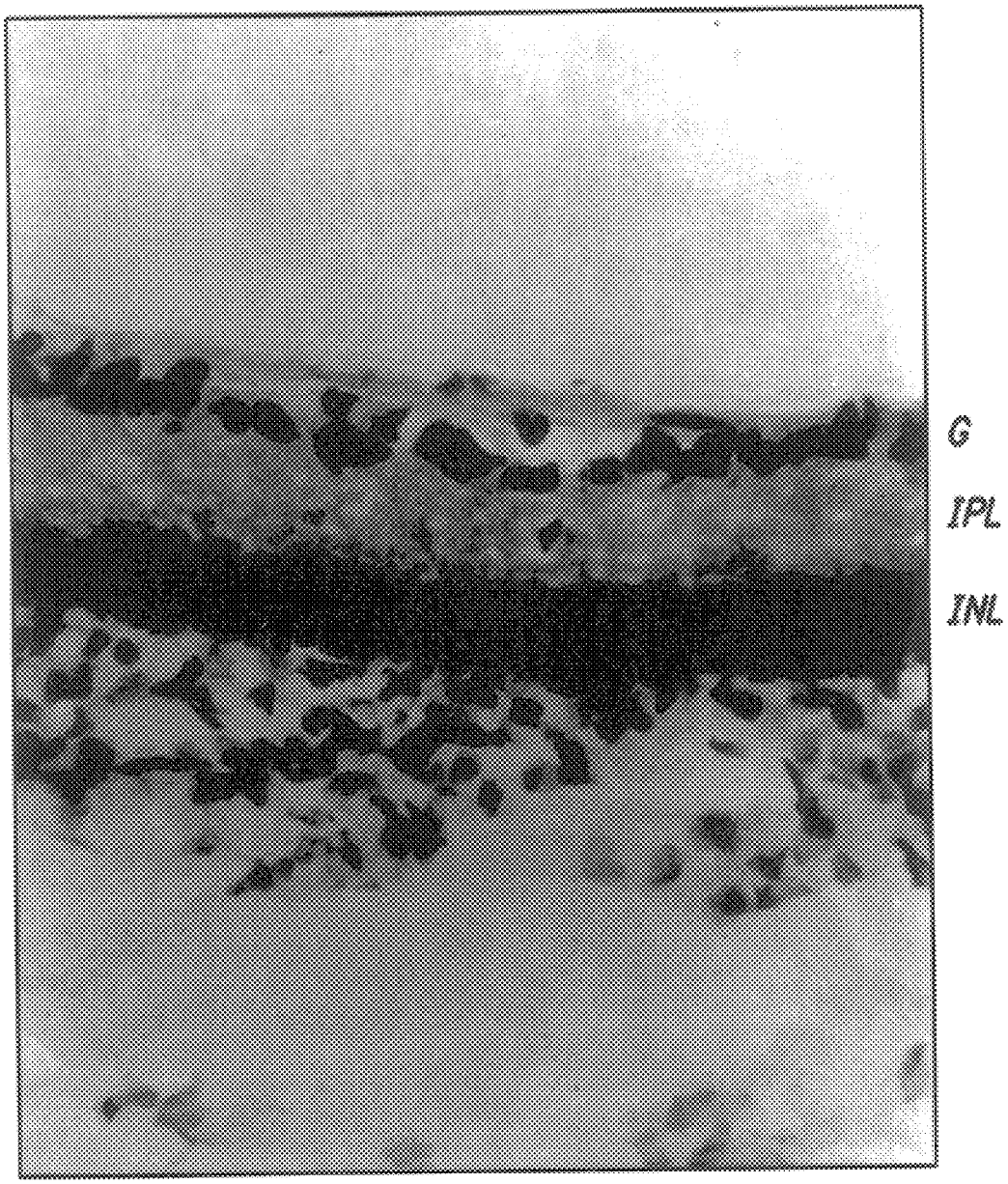
FIG. 2 is a photograph of a blinded rat retina following constant illumination as set forth in Example 1.

FIG. 1 is a photograph of a cryostat section of normal rat retina. FIG. 2 is a photograph of a cryostat section of a rat retina following constant illumination which destroys the photoreceptor (outer nuclear) layer while leaving other retinal layers and cells largely intact. In these and subsequent figures, the retina or layers thereof, e.g., the ganglion cell layer ("G"), inner plexiform layer ("IPL"), inner nuclear layer ("INL"), outer plexiform layer ("OPL"), outer nuclear layer ("ONL"), inner segments ("IS"), outer segments ("OS"), and retinal pigment epithelium ("RPE"), are shown, respectively, from top to bottom.

Figure 3:
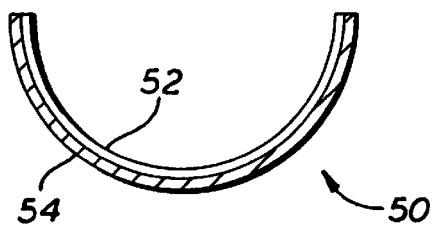
FIG. 3 is a schematic of a donor retina.

Referring now to FIG. 3, a photoreceptor graft for implantation through an incision smaller than the width of the graft in sheet-like form is prepared in accordance with a method of the present invention. The graft, however, may comprise other implantable material such as other retinal cells, antiviral and antibiotic agents and/or other pharmacologic agents.

Figure 4:
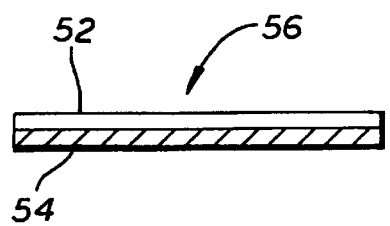
FIG. 4 is a schematic of a flattened retina.

A graft comprising photoreceptor cells is prepared by removing a donor retina 50 comprising inner retina layers 52 and a photoreceptor layer 54 from a donor eye. The donor retina 50 is flattened (FIG. 4) by making a plurality of cuts through the retina from locations near the center of the retina to the outer edges thereof (see FIG. 8). Cuts can be made in other directions if necessary.

Figure 5:
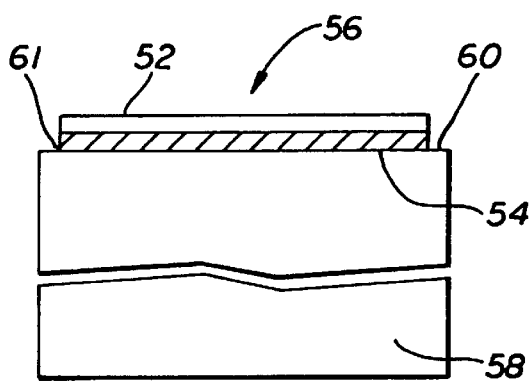
FIG. 5 is a schematic of a flattened retina mounted to a substrate.

As shown in FIG. 5, the flattened retina 56 is placed with the photoreceptor side 54 down on a gelatin slab 58 which has been surfaced so as to provide a flat surface 60 that is parallel to the blade of a vibratome apparatus. The gelatin slab 58 is secured to a conventional vibratome chuck of the vibratome apparatus. Molten four to five per cent gelatin solution is deposited adjacent the flattened retina/gelatin surface interface 61 and is drawn by capillary action under the flattened retina 56 causing the flattened retina to float upon the gelatin slab 58. Excess molten gelatin is promptly removed and the floating flattened retina 56 is then cooled to approximately 4° C. with ice-cold Ringer's solution that surrounds the gelatin block to cause the molten gelatin to gel. The flattened retina 56 is thereby adhered to the gelatin block 58.

Figure 6:
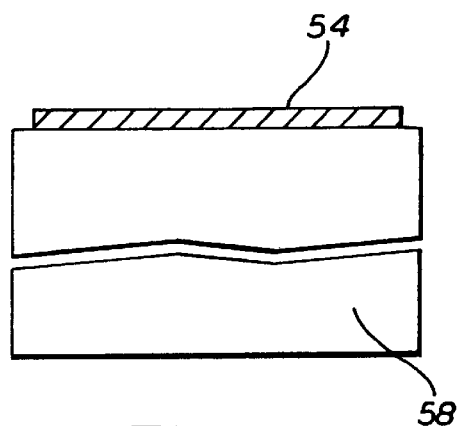
FIG. 6 is a schematic of a sectioned retina mounted to a substrate.
Figure 7:
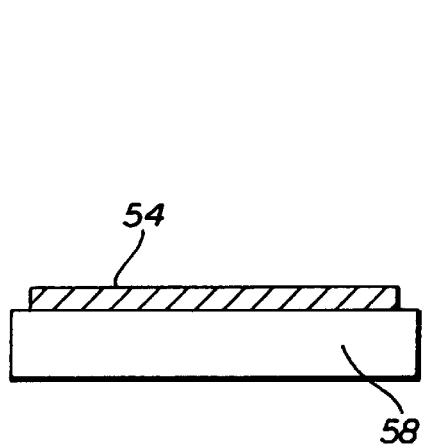
FIG. 7 is a schematic of a laminate comprising a retina section on a supporting, stabilizing substrate.
Figure 8:
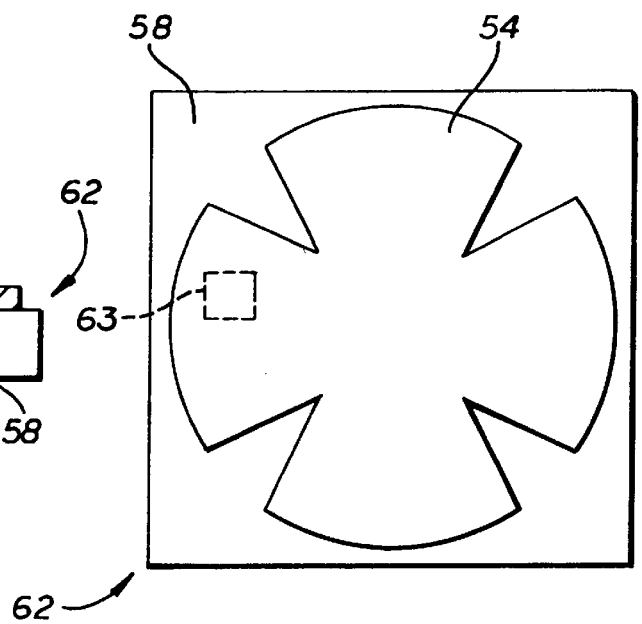
FIG. 8 is a schematic top plan view of the laminate of FIG. 7, showing a graft (dashed lines) comprising a photoreceptor cell layer and a supporting, stabilizing substrate.

As shown in FIG. 6, the inner retina portion 52 is sectioned from the top down at approximately 20 to 50 millimicrons until the photoreceptor layer 54 is reached, thereby isolating the photoreceptor layer from the inner layers of the retina, i.e., the ganglion cell layer, inner plexiform layer, inner nuclear layer, and outer plexiform layer. When the photoreceptor layer 54 is reached, the vibratome stage is advanced and a section from approximately 50 to 300 millimicrons thick is obtained as shown in FIG. 7. The thickness of this section should be sufficient to undercut the photoreceptor and form a section 62 consisting of a layer of photoreceptor cells and a thin gelatin substrate 58 adhered thereto. As shown in FIG. 8, the section 62 is cut vertically along the dashed lines to create a laminate 63.

Figure 9:
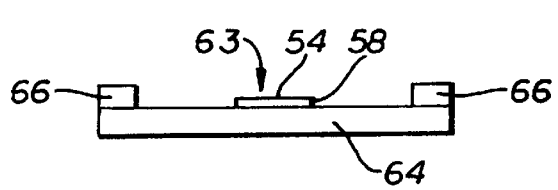
FIG. 9 is a schematic of the graft mounted on a plate formed with spacers.
Figure 10:
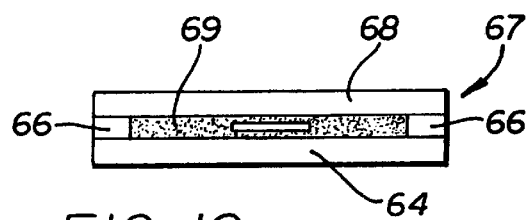
FIG. 10 is a schematic of the graft mounted on a plate infused with molten gelatin with a cover plate.

The laminate 63 is then placed onto a flat plate 64 formed with risers 66 as shown in FIG. 9. The plate 64, with the laminate 63 positioned between the risers 66, is infused with molten fifteen to twenty per cent gelatin solution to surround and cover the photoreceptor layer 54 with the gelatin substrate 58 is surrounded and covered by the molten gelatin. As shown in FIG. 10, a flat cover plate 68 is placed on top of the risers 66 to remove any excess molten gelatin and to establish the precise thickness of the graft. The height of the risers 66 can be adjusted to prepare grafts of different thicknesses.

The resulting container 67 consisting of two plates 64, 68 separated by risers 66 encasing a gelatin slab 69 with the photoreceptor layer 54 embedded therein is cooled to room temperature to cause the molten gelatin to gel and form a carrier sheet 70 encapsulating the photoreceptor layer 54. The outer segment (not shown) of the photoreceptor layer 54 faces toward one face 71 of the carrier sheet 70.

Figure 11:
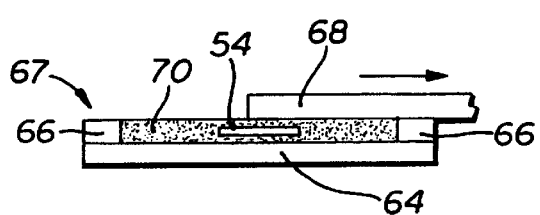
FIG. 11 is a schematic of the top plate being laterally slid off.
Figure 12:
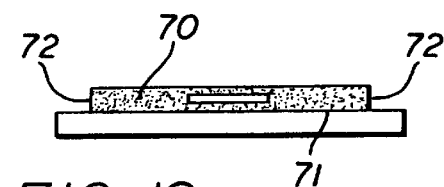
FIG. 12 is a schematic of the resulting graft.

As shown in FIG. 11, after the molten gelatin is allowed to gel, the top cover plate 68 of the laminate is carefully removed by sliding the plate laterally away from the risers 66 so as to prevent any tearing of the gelatin carrier sheet 70 and layer of photoreceptors 54. The risers 66 are likewise removed to expose the carrier sheet 70. To further reduce the risk of tearing the gelatin carrier sheet 70 upon removal of the top cover plate 68 the top cover plate can be wrapped in a TEFLON film (not shown) so that the bottom surface of the cover plate has a smooth layer of film affixed thereto. The top cover plate is removed by unwrapping the film on the upper surface of the cover plate and lifting the plate from the risers 66. The TEFLON film is then carefully peeled from the gelatin carrier sheet 70. Immersion in a dissecting fluid (such as an aqueous solution) can facilitate peeling.

Figure 13:
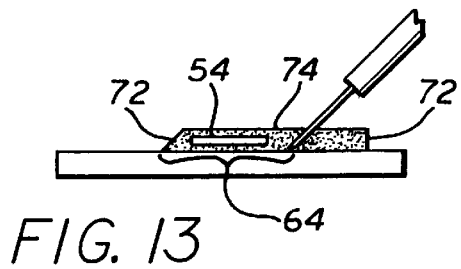
FIG. 13 is a schematic of the graft being skived.

Opposite ends 73 of the carrier sheet 70 are cut vertically to a size appropriate for transplantation. As shown in FIG. 13, opposite sides 72 of the carrier sheet 70 can be skived—cut at obtuse and acute angles relative to the top and bottom surfaces of the gelatin slab—to produce a graft 74 having approximately parallel sides. The skived sides 72 of the graft 74 facilitates the sliding of one side 72 of the graft over the other side. The surface of the graft 74 should have a surface area greater than about 1 square millimeter, preferably greater than 4 square millimeters or as large as may be practically handled within a surgical instrument for implantation of the graft through an incision in a host eye. Thus constructed, the graft 74 may subtend a considerable extent of the retinal surface.

Figure 15:
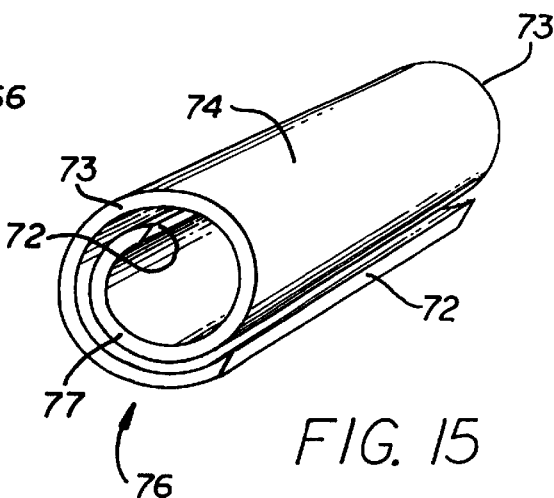
FIG. 15 is a perspective view of a volute.
Figure 14:
FIG. 14 is a schematic of the skived graft being removed from the plate for transplantation.

To prepare the graft for insertion into the eye, the graft 74 is removed from the plate 64 (FIG. 14) and formed into a volute 76 (FIG. 15) having overlapping sides 72 and convolutions 77. The convolutions 77 of the volute 76 are free of one another in the sense that the convolutions do not impede the volute from subsequent uncoiling. Although it is not presently preferred, the sides 72 of the volute 76 do not necessarily need to overlap; any coiled configuration of the graft 74 whereby the diameter of the volute is less than the distance between the sides 72 of the uncoiled, sheet-like graft and whereby the photoreceptor layer 54 is not damaged may be prepared in accordance with the present invention.

The thickness of the graft 74 comprising the sectioned flattened retinal tissue 54 and the carrier sheet 70 as discussed above is only approximate and will vary as donor material varies. In addition, sectioning may be facilitated and vibratome thickness further calibrated from histological measurements of the thickness of the retina, thereby providing further guides to sectioning depth. Appropriate sectioning thicknesses or depth may be further determined by microscopic examination and observation of the sections.

The gelatin carrier sheet 70 adds mechanical strength and stability to the easily damaged photoreceptor layer 54. As a result, the flattened retinal tissue 54 is less likely to be damaged and is more easily manipulated during the transplantation procedure. Gelatin is presently preferred as an encapsulant because of its flexibility, pliability, ability to dissolve at body temperature and apparent lack of toxicity to neural tissue upon dissolution. However, other compositions such as auger or agarose which also have the desirable characteristics of gelatin may be substituted. Significantly, gelatin has not been found to interfere with tissue growth or post-transplant interaction between the graft 74 and the underlying retinal pigment epithelium. Gelatin is also presently preferred as an adhesive to laminate the retinal tissue 54 within the encapsulant. However, other compositions, including lectins such as concanavalin A, wheat germ agglutin, or photo reactive reagents which gel or decompose upon exposure to light and which also have the desirable characteristics of gelatin may be substituted as the adhesive.

Advantageously, the gelatin carrier sheet 70 or other encapsulant may additionally serve as a carrier for any of a number of trophic factors such as fibroblast growth factor, pharmacologic agents including immunosuppressants such as cyclosporin A, anti-inflammation agents such as dexamethasone, anti-angiogenic factors, anti-glial agents, and anti-mitotic factors. Upon dissolution of the encapsulant, the factor or agent becomes available to impart the desired effect upon the surrounding tissue. The dosage can be determined by established experimental techniques. The encapsulant may contain biodegradable polymers to act as slow release agents for pharmacologic substances that may be included in the encapsulant.

As an alternative to mechanical, e.g., microtome, sectioning, the donor retina 50 may be chemically sectioned. Specifically, it is known that neurotoxic agents such as kainic acid or anoxia are toxic to cells in all retinal layers 52 except to photoreceptors and Müller cells. Therefore if the donor retina 50 is treated with an appropriate neurotoxic agent the photoreceptor layer 54 can be isolated. This technique has the advantage of maintaining the retinal Müller cells (which are relatively insensitive to kainic acid and anoxia) with the photoreceptor cells 54. Since it is known that Muller cells help maintain photoreceptor cells 54 (both biochemically and structurally) the isolation of Müller cells along with the photoreceptor cells could be advantageous.

If desired, the graft 74 may contain retinal pigment epithelial cells. Because the RPE is tenuously adherent to the retina, mechanical detachment of the retina from a donor eye ordinarily will cause the RPE to separate from the retina and remain attached to the choroid. However, through the use of enzymatic techniques such as those described in Mayerson et al., *Invest. Opthalmol. Vis. Sci.* 25: 1599–1609, 1985, the retina can be separated from the donor eye with the RPE attached. Alternatively, implants comprising a monolayer of RPE cells can be prepared by harvesting RPE cells from donor tissue and apposing the harvested RPE cells as an intact monolayer to a non-toxic, flexible composition, or by seeding such a composition with a monolayer of dissociated RPE cells and allowing them to grow into a confluent layer. The flexible composition serves as a stabilizing support for the RPE cells during encapsulation and transplantation.

Grafts comprising the choroid, Bruch's membrane or a synthetic Bruch's membrane (e.g., collagen sheet on the order of 1–5 microns) may also be prepared. The choroid is stripped off of the scleral lining of the eye (with or without the RPE attached) and flattened by making radial cuts. The donor choroid may be encapsulated as previously described for the photoreceptor cells and/or combined with a photoreceptor layer 54 which has been prepared as described above to form a laminate comprising a photoreceptor layer and a choroidal layer encapsulated within a gelatin substrate and superstrate.

Figure 16:
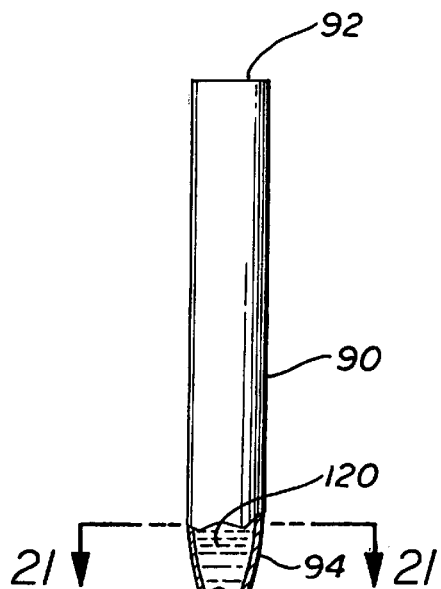
FIG. 16 is a side elevational view of an instrument for coiling and implanting the graft with the coiled graft in the funnel of the instrument.

Referring to FIGS. 16–18, there is shown a surgical instrument 78 for creating a volute 76 and implanting the volute at the transplantation site of the host eye. The surgical instrument 78 and method of this invention are particularly adapted for the isolation and transplantation of an intact sheet of cells from a donor retina to a recipient retina through an incision which is smaller than the incision that would be required for insertion of the graft 74 in its uncoiled sheet-like form and the instrument 78 and method are further characterized by the maintenance of cell organization of the transplanted tissue layer.

An embodiment of an instrument 78 for implanting an intact cellular structure 74 between the retina and supporting tissues in an eye is indicated generally in FIG. 16. The instrument 78 may be made from acrylic, glass or some other suitable material that is sterilizable. The instrument 78 comprises a tubular body 90 open at one end 92 for receiving the generally planar cellular structure 74, a tapered passage or funnel 94 for coiling the planar structure 74 into a volute 76, and a tubular tip 96 for insertion into the host eye. As shown and described herein, the instrument 78 is approximately 10 to 15 centimeters long, which is an appropriate length for making implants in rodents and lower primates. The narrow tubular tip 96 which is inserted into the incision of the eye—the eye port—must be sufficiently long to extend into the eye to reach in between the retina and the supporting sub-retinal tissue. Different lengths may be used for the narrow tubular tip 96 of the instrument 78 depending upon the procedure being employed and upon the recipient.

As shown in FIG. 21, the instrument 78 may include a ramp 99 on the inside surface of the instrument at the transition from the tubular body 90 to the funnel 94. The ramp directs one side 72 underneath the other side of the graft 74 to form volute 76. In this embodiment of the instrument 78, the side edges 72 of the carrier sheet 70 can be cut vertically, instead of skived to form graft 74. The ramp 99 prevents buckling of the graft 74 by not permitting the side edges to contact each other and can act to align the volute in a specific orientation (e.g., one edge of the volute can be maintained in a particular orientation).

As shown and described herein, the inner diameter of the instrument 78 is approximately 5 millimeters at its open end 92 and 800 microns at its tubular tip 96. The inner diameter of the tubular tip 96 must be sized to allow an intact coiled cellular structure—i.e., a volute 76—to pass therethrough for implantation without causing the convolutions 77 of the volute to create shear stress on one another and thus possibly cause damage to the photoreceptor layer 54 embedded therewithin. Thus, different tubular diameters may be used depending upon the recipient and the size of the graft 74. Furthermore, the transition in the funnel 94 from the diameter of the open end 92 to the diameter at the narrow tubular tip 96 cannot be too abrupt as to cause graft 74 to buckle. Accordingly, the slope of funnel 94 is gradual to allow for controlled coiling of the graft 74.

As shown in FIG. 18, the edge 98 of the narrow tubular tip 96 of the instrument 78 can be beveled to facilitate both the insertion of the instrument into the eye and the advancement of the tubular tip into the subretinal tissue of the eye with a minimum of trauma. Further, as shown in FIG. 20, the beveled edge 98 of the tubular tip 96 facilitates the gradual uncoiling of the graft 74 as one end of the graft is being ejected from the tubular tip. The edge 98 of the tubular tip 96 is preferably beveled at about 45°, from the top to the bottom. The narrow tubular tip 96 of the instrument 78 is preferably curved along its longitudinal axis from the edge 98 of the tubular tip to the small end of the funnel 94, as generally indicated at 100. The curvature 100 of the tubular tip 96 facilitates the manipulation of the instrument 78 within the eye; particularly the manipulation of the instrument to a position between the retina 82 and the supporting tissue 84 on the curved walls of the eye. The radius of the curvature 100 of the tubular tip 96 will depend upon the procedure and the radius of curvature of the host eye.

The instrument 78 further comprises plunger means 35 to assist the graft 74 through the narrow tubular tip 96. As shown in FIG. 18, the plunger means 85 is preferably a thin tubular plunger 86 received in the open end 92 of the tubular body 90 so that relative advancement of the plunger through the funnel 94 and into the tubular tip 96 with respect to the tubular body urges the coiled cellular structure 76 through the funnel of the tubular body and through the tubular tip of the instrument 78. To reduce damage to the fragile cellular structure 76 caused by direct contact between the plunger 86 and the cellular structure, the coiled cellular structure is protected from direct contact with the plunger 86 by a spacer made from gelfoam 102 or other soft compressible material which is inserted into the open end 92 of the tubular body 90 prior to the insertion of the plunger. The gelfoam 102 is guided to lay on top of the coiled cellular structure 76 and thereby protects the coil from direct contact with the mechanical plunger 86. Gelfoam is satisfactory because it is semi-solid and non-toxic. The plunger 86 projects a sufficient distance from the open end 92 of the tubular body 90 so that the projecting end 88 of the plunger can be manipulated even when the tubular tip 96 of the instrument 78 is in the eye. The preferred method of operating the instrument 78 is that once the tubular tip 96 with the coiled cellular structure 76 therein is properly located within the subretinal area 80 of the eye, the plunger 86 is manipulated to eject the coiled cellular structure 76 from the tubular tip 96 of the instrument. While the plunger 86 provides the greatest control over the ejection of the volute 76 into the eye, some caution must be exercised while operating the plunger because of the increased likelihood of damage to the volute 76.

Alternatively, the plunger means 85 may comprise means for applying fluid pressure (not shown) on the contents of the tubular body 90. In this case, the open end 92 of the tubular body is connected to a line connected to a source of fluid under pressure. Fluid can be selectively supplied via the line to the open end 92 of the instrument 78 to displace its contents. The fluid may be viscous, for example a 2% carboxymethylcellulose, or non-viscous. Particularly in the later case, it may be desirable to have gelfoam or some other relatively soft spacer material in the tube to act as a mechanical plunger and to separate the fluid from the cell structure being implanted. As previously discussed, gelatin is satisfactory to protect the volute because it is semi-solid and will dissolve harmlessly if it is ejected from the instrument. While the use of fluid pressure as the plunger means 85 significantly decreases the likelihood of damage to the volute 76, it also results in a significant reduction in the degree of control over the ejection of the volute 76 from the instrument 78.

As shown and described in parent application Ser. No. 07/566,996 (which is incorporated herein by reference), numerous features can be included with the instrument to facilitate a particular surgery. As shown in FIG. 17, the instrument may include a lumen 108 extending generally parallel with the instrument 78. As used herein, lumen 108 refers to any tube-like vessel, whether separately provided or formed as a passageway on the outside of the instrument 78. The lumen 108 has a distal end 110 generally adjacent the tubular tip 96 of the instrument 78, and preferably slightly advanced relative to the tubular tip. The proximal end 112 of the lumen 108 is remote from the distal end 110 and may be provided with a connector for connection with a source of fluid under pressure. Thus, the lumen 108 can eject a stream of fluid from its distal end 110 to create a fluid space ahead of the instrument 78. The tubular tip 96 of the instrument 78 follows generally in the path opened by the fluid thus minimizing direct contact of the instrument and the eye tissue. The distal end 110 of the lumen 108 may be beveled to facilitate the advancement of the instrument 78, particularly at times when fluid is not being ejected from the lumen. The end 110 is preferably beveled at about 45°. The fluid ejected from the lumen 108 may be a saline solution, or some other fluid that will not harm the delicate eye tissues. Various substances, such as anti-oxidants, anti-inflammatories, anti-mitotic agents and local anesthetics can be provided in the fluid for treatment of the eye or implanted tissue.

Depending on the type of surgery, the instrument may also include a fiber optic filament (not shown) extending generally parallel with lumen 108, and positioned between the lumen and the tubular body 90. The fiber optic filament facilitates the manipulation of the instrument 78 and the proper placement of the graft 74 in two ways: a light source can be provided at the proximal end of the fiber optic filament so that the filament provides light at the tubular tip 96 of the instrument 78, to facilitate the visual observation procedure through the pupil; alternatively, a lens could be provided at the proximal end of the fiber optic filament so that the filament can be used for direct observation at the tubular tip of the instrument. Additionally, the fiber optic filament could allow for laser-light cautery to control subretinal bleeding.

The instrument 78 can further include a second lumen (not shown) extending generally parallel with first lumen 108, and positioned between the lumen 108 and the tubular body 90. The second lumen allows for the aspiration of material from the tubular tip 96 of the instrument 78. The proximal end of the lumen can be connected to a source of suction so as to remove excess fluid and debris.

The instrument 78 can further include a pair of lead wires (not shown) terminating in an electrode at their distal ends. The electrode allows for cauterization of blood vessels. The proximal ends of the leads can be connected to a source of electrical power to seal broken blood vessels. It is possible to incorporate the leads onto the wall of the tubular body 90 of the instrument 78.

Of course, two or more of the features described with respect to the alternate embodiments could be combined, as necessitated by the particular circumstances.

The method of transplanting a volute 76 into the subretinal area of an eye comprises assembling a transplantable material such as retinal pigment epithelial tissue, choroidal tissue, Bruch's membrane and/or retinal cells 54 into a graft 74 as previously described. It will be understood that the transplantable material may be formed into a graft without the gelatin carrier sheet and still be within the scope of the present invention. Preferably, however, the graft is assembled with a carrier sheet 70. The transplantation method provides for the graft 74 to be placed in the instrument at the open end 92 of the tubular body 90 with the graft 74 engaging the interior wall of the tubular body. The graft 74 is placed, one end 73 first, in the open end 92 of the tubular body 90 so that the carrier 70 will be coiled with the outer segments of the photoreceptor layer 54 facing toward the outside of the convolutions 77 of the resultant volute 76 and so that the volute will uncoil in said subretinal area 80 with the outer segment of the photoreceptor layer facing toward the pigment epithelial layer 84 of the host eye. The tubular tip 96 of the instrument 78 is capped 118 and the tubular body 90 is filled with viscoelastic fluid 120 which facilitates the graft's progression into the tapered passage or funnel 94. The graft 74 slidably proceeds into the funnel 94 engaging the progressively narrowing tapered surface causing the graft to progressively coil. As the interior walls of the funnel 94 narrow sufficiently to cause the sides 72 of the carrier sheet 70 to make contact, one side 72 of the sheet 70 slides underneath the other side of the carrier sheet due, in part, to the carrier's skived sides. The skived sides 72 prevent any buckling of the carrier sheet 70 as the side edges make contact. In the alternative embodiment shown in FIG. 21, as the interior walls of the instrument 78 narrow sufficiently to cause the sides 72 of the graft 74 to be in proximity to each other, ramp 99 directs one side underneath the other side to begin the coiling of the volute 76. At some point in the funnel 94 the convolutions 77 of the coil 76 are sufficiently constricted so that the viscoelastic fluid 120 can no longer force the coil through the funnel. A gelfoam spacer 102 is placed on top of the coil 76, a bulb 104 is placed on the open end 92 of the instrument to create a vacuum so that the fluid 120 and the volute 76 remain in the instrument 78, and the cap 118 is removed from the tubular tip 96 of the instrument 78. A syringe 106 can be inserted through the bulb 104 to inject more fluid 120 as required. The plunger 86 is inserted through the bulb 104 into the open end 92 of the tubular body 90 and manipulated to be in contact with the gelfoam spacer 102. The plunger 86 is carefully advanced to force the graft 74 through the funnel 94 to further coil the graft into a volute 76 and into and through the curved path 100 of the tubular tip 96.

The host eye is prepared so as to reduce bleeding and surgical trauma. A scleral pars plana surgical approach to the subretinal space is preferred (FIG. 20), but other approaches, such as transcorneal and trans-scleral, may be used. A small incision (about 0.75 mm–2.0 mm) is made in the pars plana large enough to insert surgical instrument 78. Following vitrectomy, the eye can be cooled by infusion of cooled balanced salt solution through a second pars plana port into the vitreal cavity of the eye 112, to avoid dissolution of the carrier sheet 70 of the volute 76 during the surgical procedure. A portion of the retina 82 at the site of implantation is raised away from the pigment epithelial cell lining 84 by making an incision 122 in the retina and infusing balanced salt solution in the subretinal area to form a bleb 80 at the implantation site of the retina 82. If the instrument 78 includes a lumen 108, the retina 82 may be detached by the gentle force of a perfusate such as a saline-like fluid, carboxymethylcellulose, or 1–2% hyaluronic acid ejected from the lumen to create a bleb 80. Advantageously, the fluid may additionally contain anti-oxidants, anti-inflammation agents, anesthetics or agents that slow the metabolic demand of the host retina 82.

The instrument 78 with the volute 76 at its tubular tip 96 is inserted through the pars plana port, through the vitreal cavity and into the subretinal space. As illustrated in FIG. 20, the instrument 78 is then manipulated so that the edge 98 of the tubular tip 96 is in line with the incision 122 of the bleb 80. The entire tip 96 of the instrument 78 is inserted in the bleb 80 and the volute 76 is ejected by carefully advancing the plunger. The volute 76 is ejected from the beveled edge 98 of the tubular tip 96 and uncoils under its inherent uncoiling memory as it is ejected from the bevelled edge so that the outer segments of photoreceptor layer 54 is facing the pigment epithelial layer 84. If the volute 76 does not uncoil entirely, micro picks can be used to completely uncoil the graft 74.

The bleb 80 is then deflated by evacuation of fluid within the bleb or by tempanade so that the graft 74 is held in a sandwich-like arrangement at the desired position by the retina 82 and pigment epithelial cell lining 84. The incision 122 of the bleb 80 may be closed cauterly. The gelatin carrier sheet 70 dissolves when it reaches normal body temperature. The edges of the scleral incision are abutted after removal of the forceps and sutured using standard opthamalogic procedures.

As shown and described in parent application Ser. No. 07/566,996, a trans-choroidal, scleral and corneal surgical approach may be used as an alternative to the pars plana approach described above. Except for the point of entry, the surgical technique is essentially the same as outlined above. In view of the above, it will be seen that the several objects of the invention are achieved and other advantages attained.

As various changes could be made in the above surgical instruments, compositions of matter and methods without departing from the scope of the invention, it is intended that all matter contained in the above description or shown in the accompanying drawings shall be interpreted as illustrative and not in a limiting sense.

What is claimed is:

1. An implement for the formation of a volute comprising a tubular body open at one end and having a funnel at its other end whereby a graft is entered one end first in the tubular body at the open end thereof and fed along the body into and through the funnel, engagement of the graft as it is fed through the funnel with an interior surface of the funnel causing the graft to coil into the volute, the volute exiting from a small end of the funnel.

2. The implement of claim 1 wherein the implement for the formation of a volute is insertable in the subretinal area of an eye for implantation of the graft.

3. The implement of claim 2 wherein the implement further comprises a tubular tip extending from the small end of the funnel, and wherein the tip is insertable through a standard size incision into the eye, the volute, formed in the funnel, passing through the tip into the subretinal area of the host eye.

4. The implement of claim 3 wherein the tubular tip comprises a bevelled edge.

5. The implement of claim 3 wherein the implement further comprises a ramp to facilitate the coiling of the graft into the volute.

6. The implement of claim 3 wherein the instrument further comprises plunger means for ejecting the volute from the tubular tip of the implement.

7. The implement of claim 6 wherein the plunger means comprises a plunger for ejecting the volute from the tubular tip of the implement.

8. The implement of claim 6 wherein the plunger means comprises fluid pressure means for ejecting the volute from the tubular tip of the implement.

9. The implement of claim 6 wherein the tubular tip is curved along its longitudinal axis.

* * * * *